United States Patent [19]
Rose

[11] Patent Number: 5,275,615
[45] Date of Patent: Jan. 4, 1994

[54] MEDICAL INSTRUMENT HAVING GRIPPING JAWS

[76] Inventor: Anthony Rose, 741 Lakefield Rd. Suite G, Westlake, Calif. 91361

[21] Appl. No.: 943,782

[22] Filed: Sep. 11, 1992

[51] Int. Cl.$^5$ ............................................. A61B 17/28
[52] U.S. Cl. ..................................... 606/208; 81/99; 606/207
[58] Field of Search ..................... 606/205–; 128/750–; 604/22; 81/345, 346, 347, 348, 349, 350, 365, 364

[56] References Cited

U.S. PATENT DOCUMENTS

| | | | |
|---|---|---|---|
| 720,385 | 2/1903 | Storle | 81/99 |
| 4,712,545 | 12/1987 | Honkanen | 606/208 |
| 4,898,157 | 2/1990 | Messroghli et al. | 606/208 |
| 5,176,699 | 1/1993 | Markham | 606/208 |

Primary Examiner—Stephen C. Pellegrino
Assistant Examiner—William Lewis
Attorney, Agent, or Firm—Roger A. Marrs

[57] ABSTRACT

A medical instrument as a forcep with tissue-gripping jaws is disclosed herein having pivotal handles carried on an instrument body from which an elongated tube projects enclosing a push-pull rod. The rod carries a pivotal jaw arrangement and outwardly projecting from the tube for tissue grasping or gripping purposes. The other end of the rod is coupled to the handle for actuation of the jaw arrangement by either push rod or pull rod functioning. A spherical piston or rack and pinion gear interconnects the rod end with the jaw arrangement and a rod travel limit stop is operably connected between the handle, rod and instrument body. The jaw arrangement includes a pair of members having opposing wavy and serrated surfaces operably to open and close to retain tissue as the instrument is manipulated by medical personnel.

7 Claims, 3 Drawing Sheets

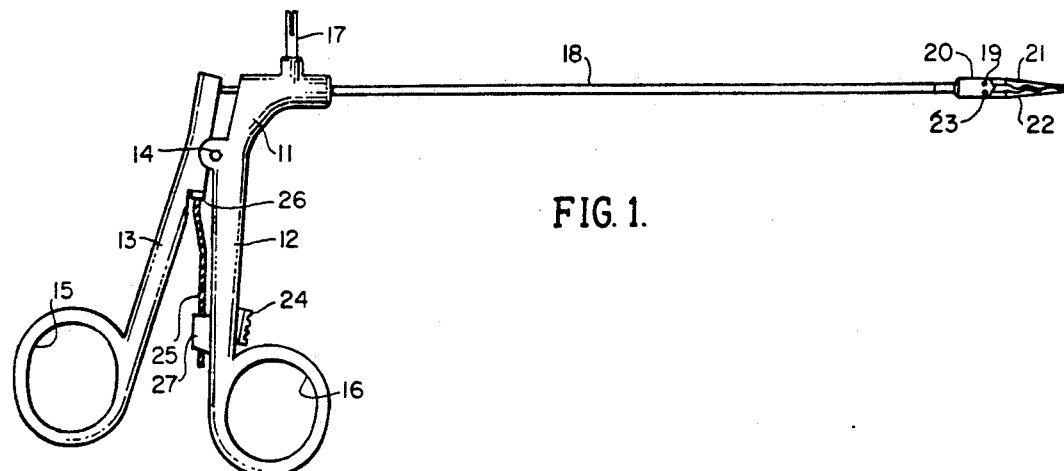
FIG. 1.
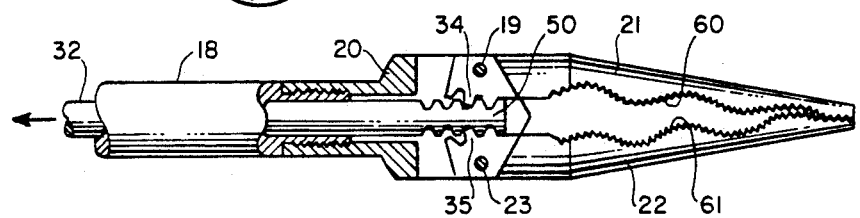
FIG. 2.
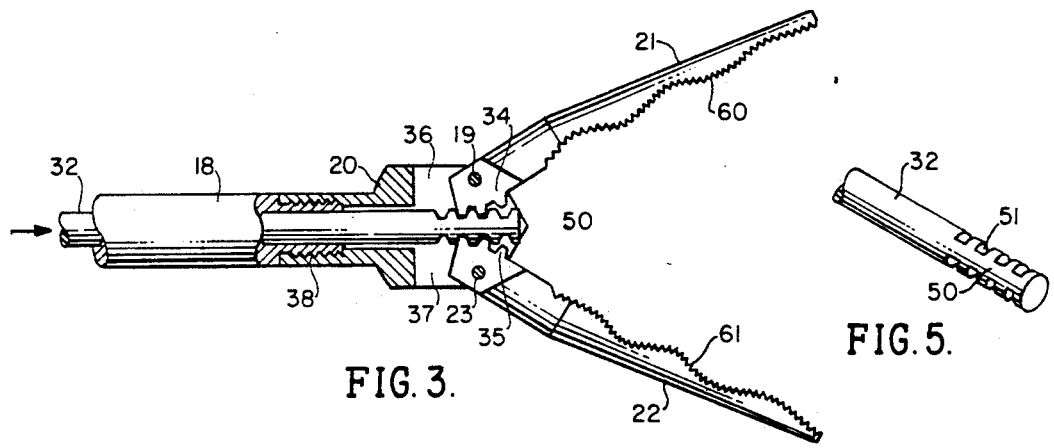
FIG. 3.
FIG. 5.
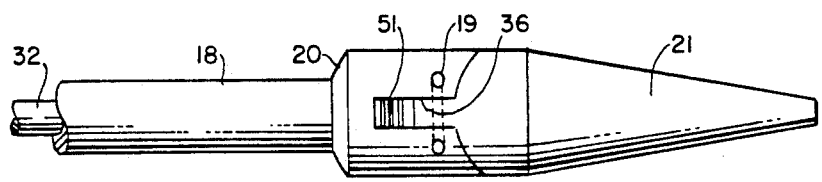
FIG. 4.

MEDICAL INSTRUMENT HAVING GRIPPING JAWS

BACKGROUND OF THE INVENTION

1. Field of the Invention

The present invention relates to the field of medical instruments, and more particularly to a novel surgical instrument having a hand-operated jaw arrangement adapted to grasp or grip a variety of articles or substances. In one application, the surgical instrument is employed to facilitate the removing of animal or human tissue. In this sense, tissue is to comprise skin, cartilage or any other cellular animal growth.

2. Brief Description of the Prior Art

It is the conventional practice for medical practitioners, surgeons or the like to utilize instruments to remove tissue from animal or human beings. The instrument is utilized to remove tissue from an inaccessible region of the body as through a natural body opening or through a surgically provided opening within the human or animal body. Such a common type of an instrument utilizes a pair of jaws with one of the jaws being movable with respect to the other jaw. The movable jaw is to be movable within a cavity of the fixed jaw. Around the fixed jaw a cutting edge is sometimes provided and during movement of the movable jaw within the fixed jaw, the tissue located therebetween is severed and this becomes located within the cavity. The medical instrument is then removed from the body and the severed tissue removed with the instrument.

Problems and difficulties have been encountered when employing such conventional instruments because of the space required for use of the instrument. It is desirable to have the instrument as small in size and physical area as possible and as small in cross-section as possible. At the present time, a typical dimension in cross-section would be no more than ½ to 1 centimeter. When dealing with such small dimensions, the instrument is fragile and even though constructed of metal, will sometimes bend, break or easily fatigue so that it is subsequently damaged. Frequently, the instrument breaks and this is extremely undesirable since such instruments are relatively expensive pieces of equipment. There is also the possibility that a broken portion of the instrument could be separate from the main portion of the instrument and become lodged in the body cavity. This requires utilization of other instruments to remove the broken piece or possibly expanding the surgical procedure in order to remove broken instrument pieces.

Furthermore, the precise opening and closing of the jaw arrangement is critical and control of push or pull rods for expanding the jaws is necessary so that the surgeon has the required control of the instrument. Furthermore, it is extremely helpful to the surgeon to be able to cauterize the area in which the surgery is being performed and conventional instruments do not provide for achieving this procedure simultaneously with the withdrawal of tissue.

Problems with prior jaw arrangements are that they often do not provide suitable grasping or gripping surfaces for holding the removed tissue. Slipping or dropping of the tissue sometimes results which should be avoided.

Therefore, a long-standing need has existed to provide a surgical instrument which is constructed of a small cross-sectional size that is of high strength and construction so as to minimize the possibility of breakage. Means for cauterizing the wound or surgical area is desirable as well as providing a jaw arrangement with non-slip grasping surfaces to provide position retention of gripped tissue.

SUMMARY OF THE INVENTION

Accordingly, the above problems and difficulties are obviated by the present invention which provides a novel medical instrument for grasping or gripping portions of the human body which comprise an instrument body for supporting one end of an elongated tube through which a push-pull rod is reciprocally carried for movement therethrough. One end of the rod includes a geared arrangement for actuating a jaw arrangement upon the actuation of a handle lever pivotally mounted on the instrument body and connected to the end of the rod opposite to its end carrying the jaw arrangement. In one form of the invention, the gear arrangement includes a rack and pinion means or a spherical piston gear having internal teeth in engagement with teeth arranged in a semicircle on the jaw arrangement. Anti-slip means are carried on the jaw arrangement to grasp the tissue and an electrode is carried on the instrument body and is insulated from the tube so that electrical energy may be safely provided to the rod and the jaw arrangements for effecting a cauterization procedure. A copper-conducting pellet is introduced into a conductive chamber disposed between the end of the electrode and the insulated tubing for achieving maximum electrical conductivity during the procedure.

Therefore, it is among the primary objects of the present invention to provide a novel medical instrument which is of greatly reduced cross-sectional size and yet houses a minimum number of operating components necessary to actuate a non-slip jaw arrangement for grasping or gripping purposes.

Yet another object of the present invention is to provide a novel medical instrument having a special spherical piston gear operably connected to a jaw arrangement and operative in response to actuation of a push or pull rod so that a non-slip jaw arrangement will grasp or grip intended articles.

A further object of the present invention is to provide a novel surgical instrument of extremely small size in cross-section which will permit the surgeon to grasp or grip tissues during the procedure with a non-slip, wavy surface jaw arrangement.

A primary object resides in the provision of a non-slip jaw arrangement having opposing wavy and serrated or knurled gripping surfaces which mate when closed to provide a positive grip about grasped tissue.

Yet a further object of the present invention is to provide a novel medical instrument having the ability to mount and operate a minimum number of parts with an extremely small volume area and of small cross-sectional dimension.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood with reference to the following description, taken in connection with the accompanying drawings in which:

FIG. 1 is a side elevational view of the novel medical instrument incorporating the present invention;

FIGS. 2 and 3 are enlarged cross-sectional views of the gearing and jaw arrangement employed in the embodiment shown in FIG. 1;

FIG. 4 is a top plan view of the jaw arrangement shown in FIG. 2;

FIG. 5 is a front perspective view of a reciprocal actuator employed in the version shown in FIGS. 2 and 3;

DESCRIPTION OF THE PREFERRED EMBODIMENT

Figure 10:
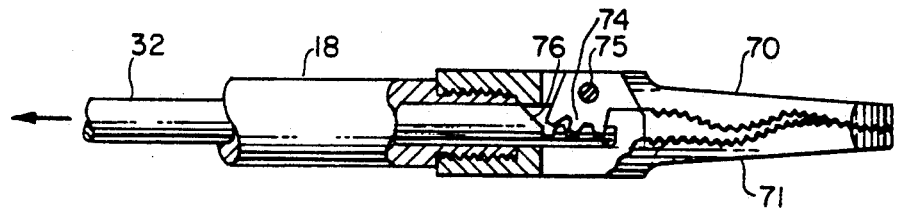
Figure 11:
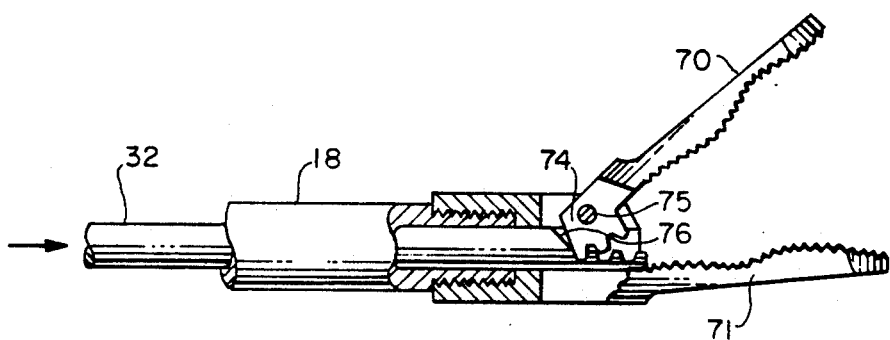
FIG. 11 is a top plan view of the jaw arrangement shown in FIG. 9.
Figure 12:
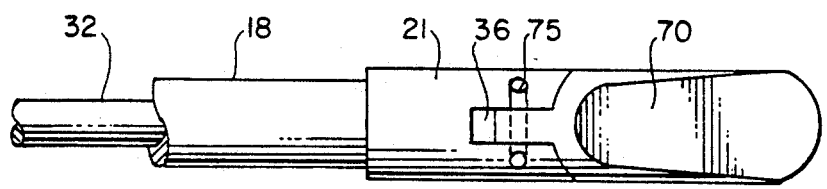
FIG. 12 is a front perspective view of the version shown in FIGS. 7 and 8.
Figure 13:
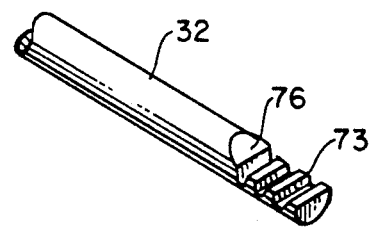
FIG. 13 is a perspective view of the rod employed in the version shown in FIGS. 10-13 inclusive.

Referring to FIG. 1, an instrument body 11 is provided having a downwardly depending fixed member 12 serving as one portion of a handle, while the other portion is represented by a handle lever 13 pivotally mounted to the body by means of a pivot connection 14. The terminating ends of the respective handle portions 12 and 13 are provided with closed loops 15 and 16 through which the user's fingers may be inserted during the use of the instrument. The instrument further includes an electrode 17 carried on the instrument body 11 and insulated therefrom. Outwardly projecting from the body 11 and normal to the electrode 17 is an elongated tube 18 terminating in a fitting 20 which houses a jaw arrangement having pivoting jaws 21 and 22 operable about pivots 19 and 23. Throughout this specification, it is to be understood that the jaw arrangement may include a pair of jaws which pivot with respect to one another or may relate, as in FIG. 10, to a stationary jaw having the other jaw of the pair moving back and forth with respect to the stationary jaw. FIG. 1 also illustrates a stop means for holding the jaw arrangement in either an open, a closed, or a midway position, and such a limit stop means includes a finger-operated button 24 which engages with a cable 25 fixed at one end to the pivoting handle lever 13. Numeral 26 illustrates the securement of the cable end to the handle lever 13, while the opposite end of the cable is slidably mounted through a block 27.

Referring now to FIGS. 2 and 3, a version of jaw arrangement is illustrated in which the jaws 21 and 22 are activated by means of a bar 50 carried on the extreme end of a rod 32 and which moves in a reciprocal manner along the central longitudinal axis of the tube 18. The bar includes a plurality of openings and is more clearly illustrated in FIG. 5 wherein a central opening is indicated by numeral 51. The teeth 34 and 35 of the jaws 21 and 22 are aligned to mesh with the opening in the bar 50 as the rod 32 is pushed or pulled. As shown in FIG. 2, the rod is pulled rearwardly to close the jaws, while in FIG. 3, the rod is pushed to open the jaws. In FIG. 4, it can be seen that a pair of pivots 19 and 23 are employed about which the jaws 21 and 22 rotate respectively.

FIGS. 3 and 4 show that the body 20 includes upper and lower slots 36 and 37 through which the tail end, of reduced thickness, of each jaw 21 and 22 moves as the jaws are positioned between their open and closed positions. A bearing sleeve 38 supports the rod 32 as it moves through the tube.

The jaw arrangement 21 and 22 included an improved gripping means taking the form of wavy opposing surfaces 60 and 61. The wavy aspect of both surfaces is shaped to conform with each when closed; however, FIG. 2 shows that the rear of closure is wide apart while the tips of the jaws engage. Tissue is generally interposed between the jaw surfaces and slippage is further prevented by providing serrations or knurled grooves on the surfaces. Therefore, a positive, non-slip surface is provided.

Figure 6:
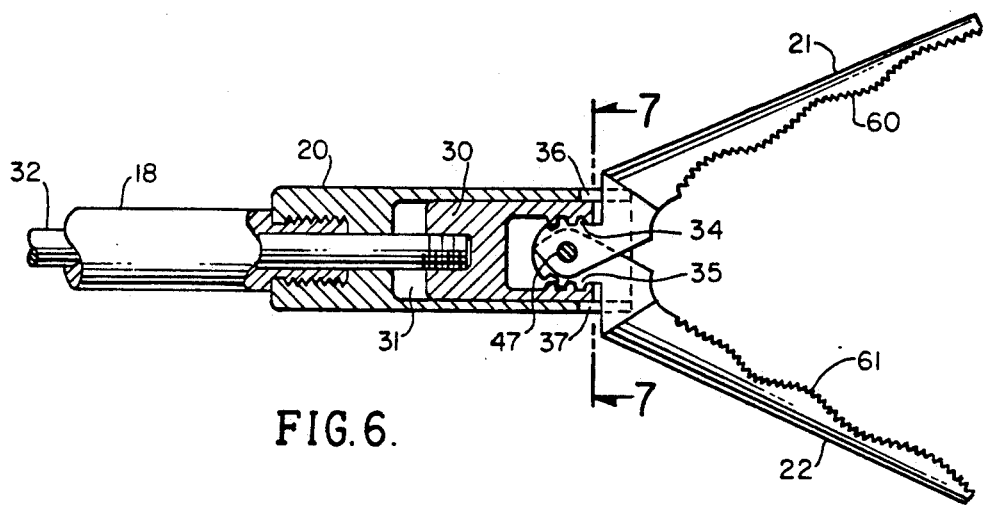
FIG. 6 is another gear arrangement for operating the jaw arrangement that may be substituted for the arrangement shown in FIGS. 2 and 3 with respect to the instrument shown in FIG. 1.
Figure 7:
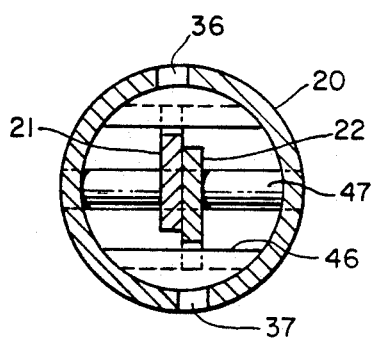
FIG. 7 is a transverse cross-sectional view of the jaw arrangement shown in FIG. 6 as taken in the direction of arrows 7—7 thereof.

Another version is shown in FIGS. 6 and 7 wherein it can be seen that the tube fitting 20 houses a piston gear 30 that reciprocates within a compartment 31 as a rod 32 is moved back and forth. One end of the rod is attached to the end of the handle lever 13 by means of a connecting element, while the other end of the rod is threadably connected to the reciprocating piston gear 30. The respective jaws 21 and 22 of the jaw arrangement include gear teeth arranged in a semicircle, that are engaged with grooves provided in the open end of the piston gear 30. Teeth 34 are carried on jaw 21 while teeth 35 are carried on jaw 22. A slot 36 is provided in the side of the piston gear 30 through which the pivot pin not only permits the jaws 21 and 22 to separate and be drawn together as the piston gear is moved within the chamber 31, but the pivot 23 prevents rotation of the piston gear or the jaws.

Figure 8:
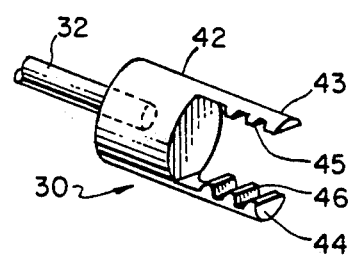
FIG. 8 is a front perspective view of the novel spherical piston gear used in the embodiment illustrated in FIG. 6.

FIG. 7 shows that the respective jaws 21 and 22 pass through slots 36 and 37 provided in the tube fitting 20 as the jaw arrangement is operated by the actuating rod 32. The respective jaws 21 and 22 are operated by means of a spherical piston gear 30 operating within a chamber 31 defined in the fitting 20. The rod 32 is pushed in order to open the jaws, as illustrated in FIG. 6, and pulled forwardly in order to close the jaws. The fitting 20 is threadably carried on the end of the tube 18, and the piston gear 30 is more clearly illustrated in FIG. 8.

In this latter FIGURE, it can be seen that the gear includes a cylindrical body 42 having outwardly projecting elements 43 and 44. Each of the elements includes teeth provided on their opposing surfaces, and the teeth are represented by numerals 45 and 46 respectively. These teeth are also illustrated in FIG. 6 and it can be seen that the space provided between the teeth accommodates placement of a pivot pin 47 about which the respective jaws 21 and 22 rotate as their semicircular teeth mesh with the teeth 45 and 46 in response to movement of the piston gear 40.

The same wavy and serrated jaw surfaces are utilized to obtain a firm, non-slip grip on any tissue held between the jaw surfaces.

Figure 9:
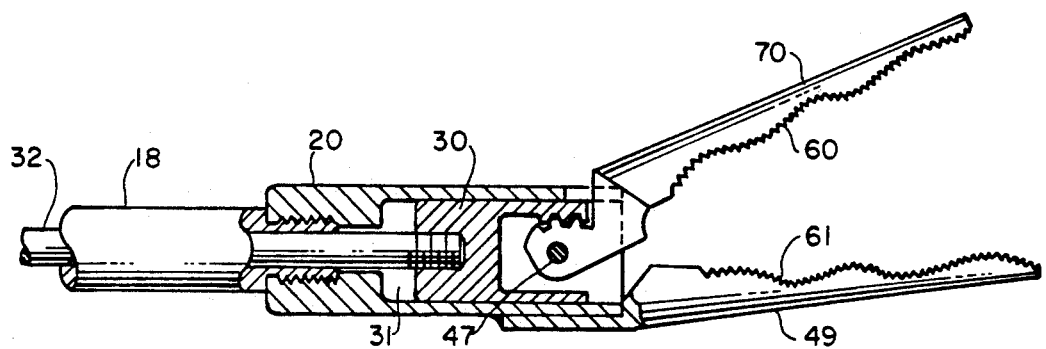
FIGS. 9 and 10 are enlarged views of another version of gear and jaw arrangement for use in the instrument shown in FIG. 1 with single jaw actuation.

FIG. 9 is another version wherein jaw 70 is movable while a fixed or stationary jaw 49 is immobile. The actuation means for moving the single jaw is the same as described with respect to the embodiment shown in FIG. 6. The same irregular, wavy and knurled, grooved or serrated gripping surfaces are used also.

FIGS. 10-13 illustrate another version of the invention utilizing the wavy and notched or serrated grooves for gripping. Only one jaw moves about a pivot while the other jaw is stationary. Numeral 70 is a movable jaw and 71 is the stationary jaw. The rod 32 includes a grooved end 73 providing teeth that engage with the semicircular gear 74. A single pivot 75 is employed. The extreme end of rod 32 includes an angled surface 76 that slidably engages with the back-side of gear 74 on one side of the pivot. Pushing the rod forward urges the cam surface 76 to force the cam follower gear 74 to pivot. Backward movement of the rod permits the jaw 70 to drop back into engagement with stationary jaw 71.

In view of the foregoing, it can be seen that the medical instrument of the present invention provides a novel jaw arrangement which is activated by a push rod or pull rod through a spherical gear or an apertured bar gear arrangement. The push rod or pull rod is operated by pivoting of the handle lever 13 and the opening or closing of the jaws as well as any mid position of the jaws is under control of the travel stop mechanism operated by the spring-biased pushbutton 24 and the cable 25.

The jaw arrangement is extremely reduced in dimension as well as volume or surface area, and the novel gearing operably connecting the end of the rod 32 with the jaw arrangement is responsible for permitting small size and reduced dimension as well as reduced cross-section of the components.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. A medical instrument of the forcep type comprising the combination of:
   an instrument body having a downwardly extending handle portion;
   a handle lever pivotally carried on said instrument body;
   an elongated tube having one end secured to said instrument body outwardly projecting normal to said handle portion to terminate in a free end;
   a jaw arrangement with jaws having irregular opposing, grasping surfaces operable to open and close in response to movement of said handle lever;
   a gear arrangement movably coupled to said jaw arrangement; and
   an actuation rod within said tube having one end secured to said gear arrangement and its other end pivotally secured to said handle lever.

2. The invention as defined in claim 1 wherein:
   said gear arrangement comprises a spherical piston gear reciprocally operating within a gear chamber carried on said tubing free end.

3. The invention as defined in claim 2 wherein:
   said piston gear includes a body having an open-ended bore with internal gear teeth;
   said jaw arrangement includes external gear teeth disposed through said open-ended bore in mesh with said internal gear teeth.

4. The invention as defined in claim 1 wherein:
   said gear arrangement includes a rod end on said rod having aligned openings constituting rod gear teeth;
   said jaw arrangement having gear teeth in mesh with said rod end teeth;
   said jaw arrangement consisting of a pair of elongated jaws having at least one of said pair pivoted at one end to said tube so as to open and close with respect to each other in response to movement of said rod;
   said jaws provided with opposing wavy and serrated grasping surfaces arranged whereby terminating ends of said jaws engage when said jaws are closed while jaws ends carried on said tube are spaced apart.

5. The invention as defined in claim 1 wherein:
   said jaw arrangement includes a movable jaw pivotally coupled at one end with said tube and a stationary jaw fixed at one end to said tube:
   said rod end further including an angled cam surface at its terminating end adjacent to said rod gear teeth; and
   said immovable jaw having a cam follower surface adjacent to jaw gear teeth and being operable to open and close said jaws in response to linear movement of said rod within said tube.

6. The invention as defined in claim 1 wherein:
   said gear arrangement includes a cylindrical member having a paid of spaced elements;
   each element having gear teeth facing each other; and
   said jaw arrangement having gear teeth in mesh with said element gear teeth.

7. The invention as defined in claim 6 wherein:
   said jaw irregular surfaces are opposing and include a wavy surface pattern conforming in shape between said jaw surfaces so as to substantially close together to provide a positive gripping action.

* * * * *